(12) United States Patent
Gütlin et al.

(10) Patent No.: US 7,691,147 B2
(45) Date of Patent: Apr. 6, 2010

(54) INTERVERTEBRAL IMPLANT

(75) Inventors: Michael Gütlin, Pratteln (CH); Manuel Schär, Muttenz (CH)

(73) Assignee: Synthes USA, LLC, West Chester, PA (US)

( * ) Notice: Subject to any disclaimer, the term of this patent is extended or adjusted under 35 U.S.C. 154(b) by 1284 days.

(21) Appl. No.: 11/147,139

(22) Filed: Jun. 6, 2005

(65) Prior Publication Data

US 2006/0058877 A1    Mar. 16, 2006

Related U.S. Application Data

(63) Continuation of application No. PCT/CH02/00674, filed on Dec. 6, 2002.

(51) Int. Cl.
*A61F 2/44* (2006.01)
(52) U.S. Cl. ............... 623/17.15; 623/17.11; 606/90
(58) Field of Classification Search ... 623/17.11–17.16; 606/63, 320, 326, 90, 105, 251, 252, 249; 254/100–103
See application file for complete search history.

(56) References Cited

U.S. PATENT DOCUMENTS

| | | | | |
|---|---|---|---|---|
| 1,862,759 A * | 6/1932 | Morrison | ............... | 254/102 |
| 4,553,273 A * | 11/1985 | Wu | ............... | 623/23.45 |
| 4,892,546 A * | 1/1990 | Kotz et al. | ............... | 623/23.45 |
| 5,236,460 A * | 8/1993 | Barber | ............... | 623/17.15 |
| 5,458,641 A * | 10/1995 | Ramirez Jimenez | ...... | 623/17.11 |
| 5,575,790 A * | 11/1996 | Chen et al. | ............... | 606/60 |
| 5,702,455 A | 12/1997 | Saggar | | |
| 5,776,197 A * | 7/1998 | Rabbe et al. | ............... | 623/17.15 |
| 6,176,881 B1 * | 1/2001 | Schar et al. | ............... | 623/17.11 |
| 6,190,414 B1 | 2/2001 | Young et al. | | |
| 6,193,756 B1 | 2/2001 | Studer et al. | | |
| 6,296,665 B1 * | 10/2001 | Strnad et al. | ............... | 623/17.16 |
| 6,375,683 B1 * | 4/2002 | Crozet et al. | ............... | 623/17.15 |
| 6,432,106 B1 * | 8/2002 | Fraser | ............... | 623/17.11 |
| 6,491,696 B1 * | 12/2002 | Kunkel | ............... | 606/105 |
| 6,866,682 B1 * | 3/2005 | An et al. | ............... | 623/17.15 |
| 2002/0082695 A1 * | 6/2002 | Neumann | ............... | 623/17.11 |
| 2002/0082696 A1 * | 6/2002 | Harms et al. | ............... | 623/17.11 |
| 2002/0161441 A1 | 10/2002 | Lang et al. | | |
| 2006/0100710 A1 * | 5/2006 | Gutlin et al. | ............... | 623/17.15 |

FOREIGN PATENT DOCUMENTS

| | | | |
|---|---|---|---|
| DE | 91 01 603.7 | | 5/1991 |
| DE | 20109599 | * | 8/2001 |

* cited by examiner

*Primary Examiner*—Eduardo C Robert
*Assistant Examiner*—Lynnsy Schneider
(74) *Attorney, Agent, or Firm*—Stroock & Stroock & Lavan LLP

(57) ABSTRACT

An intervertebral implant comprising a lower implant part, having a central axis and an apposition section, designed to rest against the covering surface of the adjacent lower vertebra and an upper implant part comprising a bore with an internal thread, a central axis and an apposition section, designed to rest against the covering surface of the adjacent upper vertebra. Specifically, the lower and upper implant parts are secured in relation to each other against rotation about the central axis and a threaded screw with an external thread is guided in the upper implant part and connected to the lower implant part, the external thread cooperating with the internal thread. The lower and upper implant parts, and the threaded screw lie coaxially along their common central axis, the threaded screw being connected to the lower implant part so that it is axially fixed but able to rotate.

17 Claims, 4 Drawing Sheets

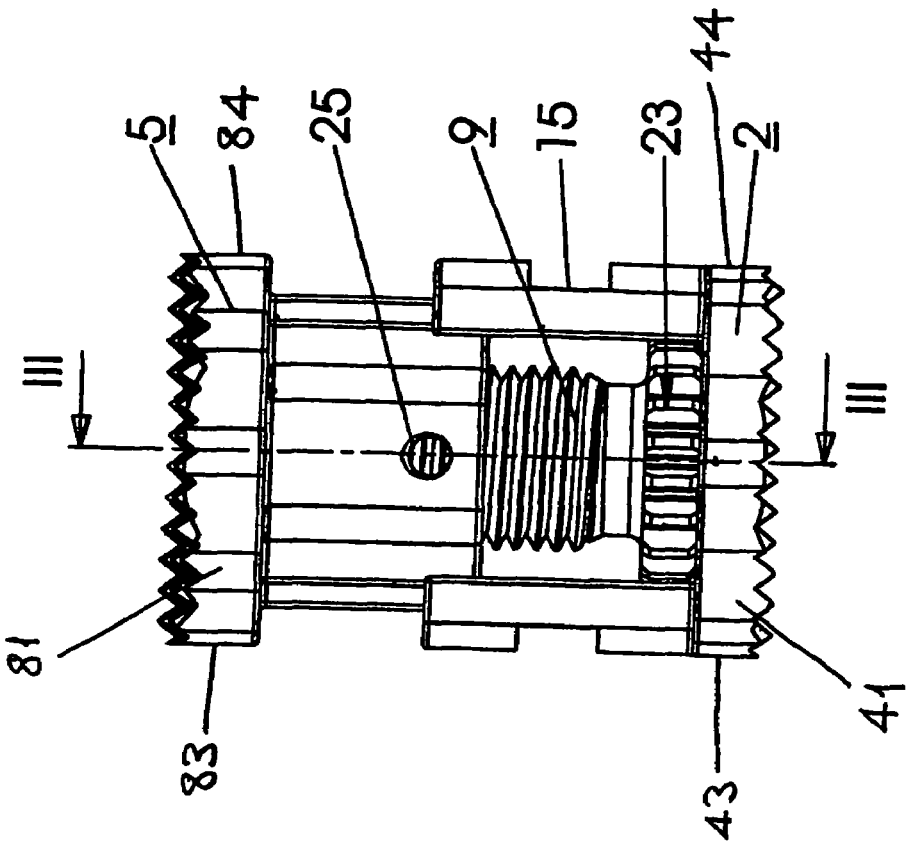
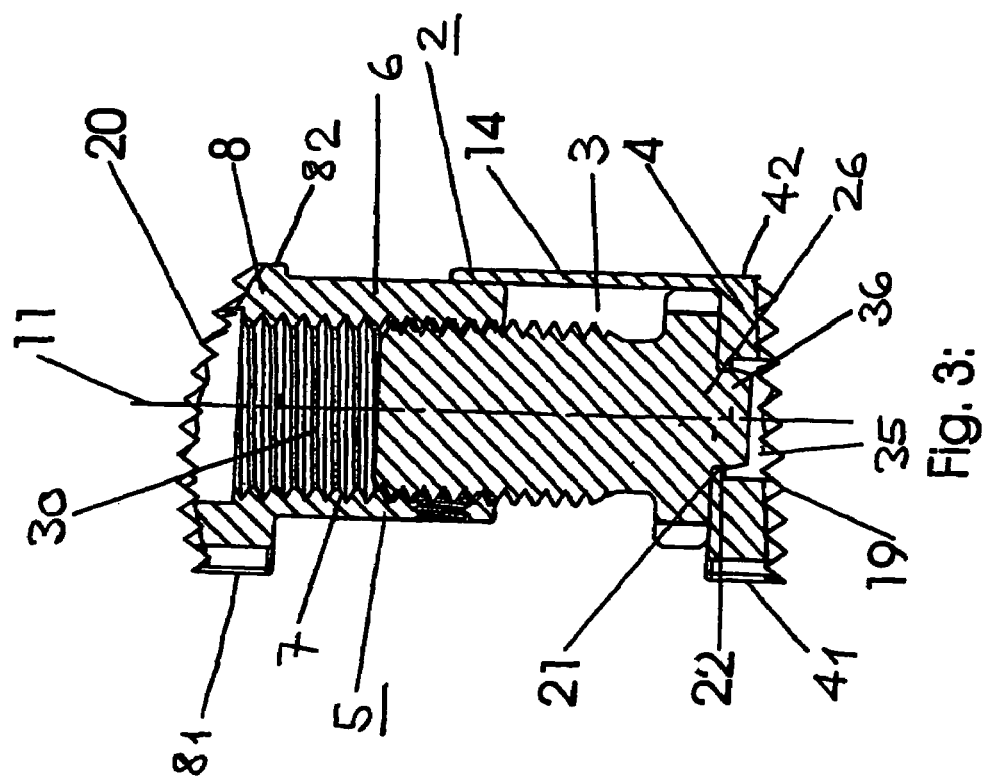

INTERVERTEBRAL IMPLANT

CROSS REFERENCE TO RELATED APPLICATION

This application is a continuation of International Patent Application No. PCT/CH2002/000674, filed Dec. 6, 2002, the entire contents of which is expressly incorporated herein by reference.

FIELD OF THE INVENTION

The invention relates generally to an intervertebral implant.

BACKGROUND OF THE INVENTION

An intervertebral implant is known from US-A 2002082695 NEUMANN. Here, the central implant part, configured as a threaded ring having an inside thread, is connected with the upper implant part that stands in the end position. The upper part of the lower implant part is structured with a conical surface that serves as an accommodation for the threaded ring. By means of a special instrument that has a bevel wheel that can be brought into engagement with the bevel wheel on the threaded ring, the threaded ring can be rotated about the central axis of the intervertebral implant and the upper implant part can be axially displaced. The threaded ring serves only as an axial stop for the upper implant part, i.e., as a support surface, so that the upper, end-position implant part can be moved axially (nut/spindle drive). The two end-position implant parts are therefore loosely mounted relative to one another, which is also indicated by the fact that axial slots are provided in one of the two implant parts, with pins affixed to the other implant part engaging in them, to secure the parts axially. Therefore this known intervertebral implant has the disadvantage that it is not secured against axial displacements before and during the operation.

In this regard, a need exists of creating an intervertebral implant that forms a compact whole, free of axial play, while maintaining the lowest possible construction height, and can be made available to the surgeon as a pre-assembled set.

SUMMARY OF THE INVENTION

The present invention may relate to an intervertebral implant comprising a lower implant part having a central axis and an apposition part intended to rest against the covering surface of the adjacent lower vertebra; an upper implant part having a bore with an inside thread and a central axis, and an apposition part intended to rest against the covering surface of the adjacent upper vertebra; and a threaded spindle, guided in the upper implant part and connected with the lower implant part, having an outside thread that interacts with the inside thread. The lower and upper implant parts are secured relative to one another to prevent rotation about the central axis. The lower and upper implant parts and the threaded spindle are disposed to be coaxial along their common central axis, and the threaded spindle is connected with the lower implant part so as to be fixed axially but movable rotationally. The distance between the two apposition parts can be changed by rotating the threaded spindle on the inside thread. The distance can also be changed in a stepless manner, the threaded spindle being fixed in place on the lower implant part so as to be fixed axially but movable rotationally, by means of a clip connection.

The advantages achieved according to the invention include simple handling, since introduction of the implant proceeds very quickly because of the distractibility of the implant and a simple set of instruments. In this way, safety is increased, and the time required for the implantation is reduced. The distance between the two apposition parts can be changed by rotating the threaded spindle on the inside thread, in stepless manner.

In a preferred embodiment, the threaded spindle may be fixed in place on the lower implant part so as to be fixed axially but movable rotationally, by means of a clip connection. This clip connection is preferably formed by a torus-shaped undercut on the lower end of the threaded spindle, and a corresponding ring-shaped bead in a bore in the lower implant part. This ensures that the two implant parts are axially held together by means of the threaded spindle. The threaded spindle preferably has a lower surface that stands perpendicular to the central axis and rests on the lower implant part.

In another embodiment, the threaded spindle comprises a gear crown that preferably lies adjacent to the lower implant part. The gear crown serves for rotational movement of the threaded spindle, by means of an instrument that can be placed at the anterior.

In yet another embodiment, the lower implant part comprises a posterior, hollow-cylinder cavity having a mantle. The mantle is preferably open at the anterior.

In yet another embodiment, the upper implant part comprises an essentially circular-cylindrical shaft, through which the bore with inside thread passes.

Preferably, the mantle of the lower implant part is provided with two slots standing perpendicular to the central axis. These slots are placed laterally on the intervertebral implant, and serve to position and support an instrument relative to the gear crown.

In yet another embodiment, it is provided that the upper implant part is secured against rotation relative to the lower implant part. This securing consists of the fact that the circular-cylindrical shaft of the upper implant part has at least one, but preferably two wedges affixed parallel to the central axis and laterally, and that the mantle of the lower implant part has at least one, but preferably two laterally placed guide slots on its inside. The wedges are axially displaceable in the guide slots, but prevent rotation of the two implant parts relative to one another.

In another embodiment, the circular-cylindrical shaft is configured in such a manner that it has a smaller circumference than the cavity, so that the two components touch one another only by means of the two wedges in the guide slots.

In yet another embodiment, the inside thread in the bore of the circular-cylindrical shaft and the outside thread of the threaded spindle are configured to be self-locking. The advantage of this embodiment consists of the fact that because of the self-locking of the thread, the implant can be distracted at any desired height, and can be held in this position without additional locking.

The pitch of the inside thread in the bore in the shaft and of the outside thread on the threaded spindle lies in the range of 0.5-1.0 mm, preferably of 0.6-0.8 mm.

Preferably, both the inside thread and the outside thread are configured to be right-hand threads. With this, the advantage can be achieved that the instrument that bears the pinion can be rotated clockwise, in usual manner, like a normal screwdriver, in order to distract the implant.

In another embodiment, two circular recesses may be placed in the anterior side surfaces of the two apposition parts, which are suitable for the accumulation of substances that support fusion, for example spongiosa.

In yet another embodiment, the two apposition parts may be configured as plate-shaped elements that stand crosswise to the central axis, having an apposition surface intended to rest against the covering surface of the adjacent vertebra.

In another embodiment, the apposition surfaces may be disposed not orthogonal to the central axis and preferably enclose an angle of 80° to 89° with the central axis. The covering plates of the vertebrae run, in a sagittal direction, not orthogonal to the axis of the vertebrae, but instead have an acute angle to it. The development of the apposition surfaces takes this anatomical situation into consideration.

Preferably, the two apposition surfaces may enclose an angle of 2° to 20° with one another.

In yet another embodiment, at least one of the two apposition surfaces, preferably the one of the upper implant, has a dome that is present in the sagittal direction. The advantage of this embodiment lies in the optimal adaptation of the apposition surfaces to the vertebrae.

In yet another embodiment, at least one of the two apposition surfaces may have a dome that is present in the coronal direction. The advantage of this embodiment lies in the optimal adaptation of the apposition surfaces to the vertebrae.

In another embodiment, a bore having a thread is placed in the shaft, crosswise to the central axis, into which a setting screw can be screwed. The setting screw serves to secure the threaded spindle from rotating about the central axis.

In yet another embodiment, the intervertebral implant is produced at least partially from a material permeable for X-rays, preferably from PEEK. This makes it possible to achieve the advantage that the fusion can be assessed more readily after the operation.

The invention and further developments of the invention will be explained in greater detail below, using the representations of several exemplary embodiments, some of them schematic.

BRIEF DESCRIPTION OF DRAWINGS

Preferred features of the present invention are disclosed in the accompanying drawings, wherein similar reference characters denote similar elements throughout the several views, and wherein:

FIG. 3 is a longitudinal section parallel to the central axis, through the embodiment of the intervertebral implant according to the invention shown in FIGS. 1 and 2;

FIG. 4 is a view from anterior of the embodiment of the intervertebral implant according to the invention shown in FIGS. 1 to 3;

DETAILED DESCRIPTION OF THE PREFERRED EMBODIMENTS

Figure 1:
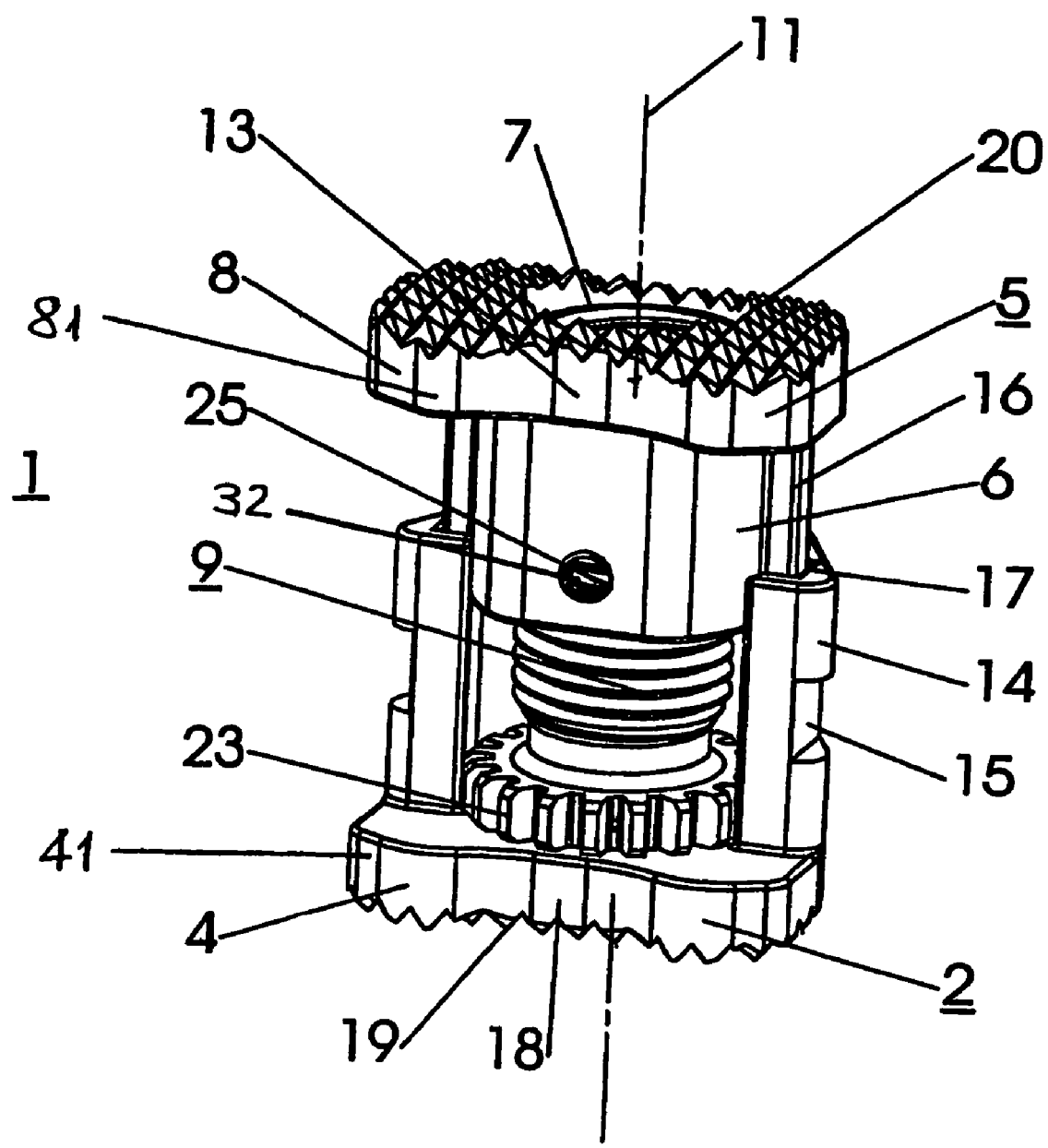
FIG. 1 is a perspective view of an embodiment of the intervertebral implant according to the invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention.

An embodiment of the intervertebral implant according to the invention is shown in FIGS. 1 to 6, which comprises a lower implant part 2 that is coaxial to the central axis 11, having an outside, lower apposition part 4, and an upper implant part 5 that is coaxial to the central axis 11, having an outside, upper apposition part 8. The lower apposition part 4 has an apposition surface 19 that stands crosswise to the central axis 11, which is intended to rest against the base surface of the vertebra adjacent towards the bottom. Analogously, the upper apposition part 8 has an apposition surface 20 that stands crosswise to the central axis 11 and is intended to rest against the base surface of the vertebra adjacent towards the top. Both apposition surfaces 19; 20 are provided with three-dimensional texturing, and have an anterior side surface 41; 81, a posterior side surface 42; 82, and two lateral side surfaces 43; 44; 83; 84, in each instance (FIGS. 3 and 4). Furthermore the upper apposition surface 20 of the upper implant part 5 has a come that is present in the sagittal direction.

Figure 2:
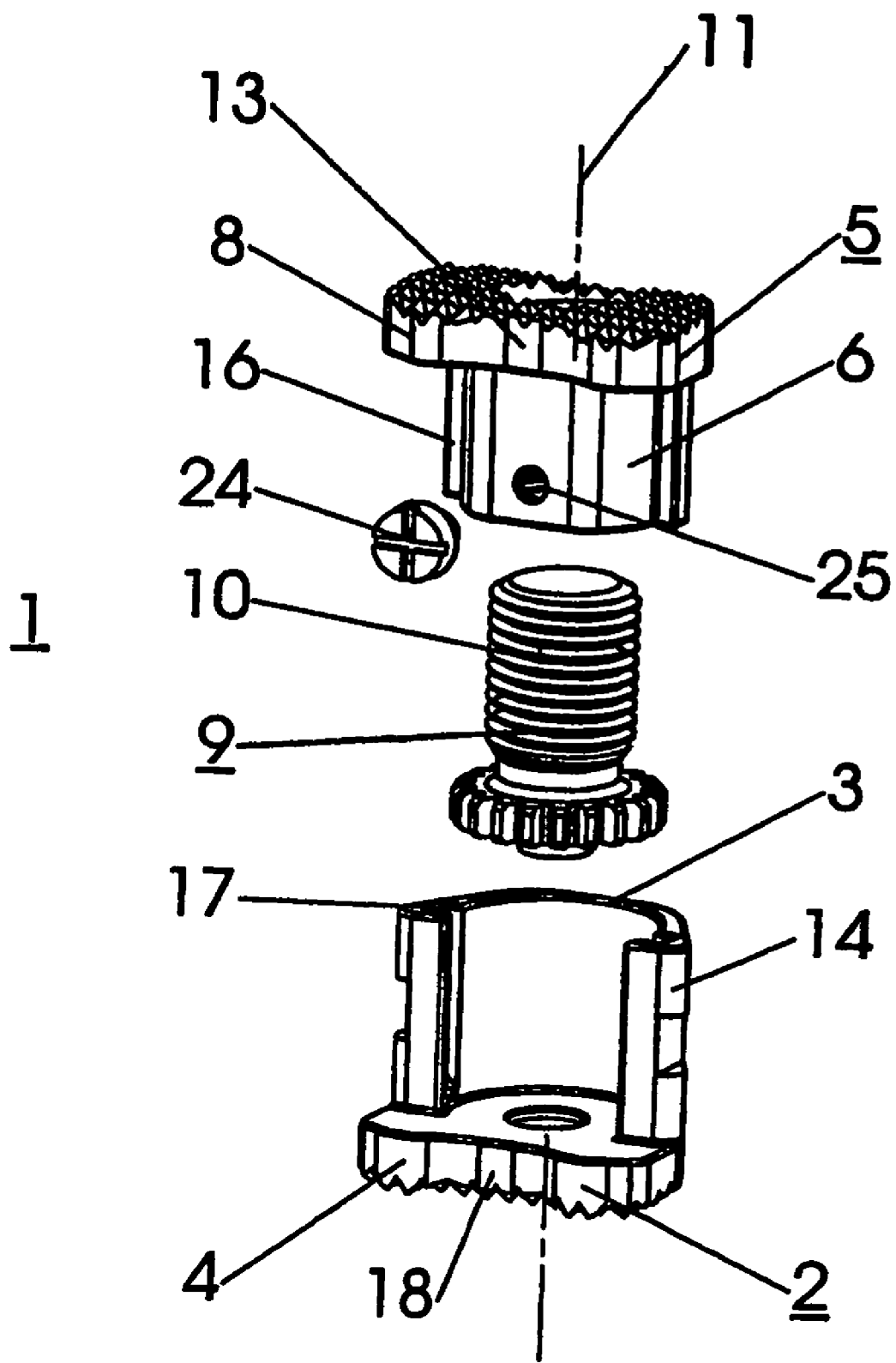
FIG. 2 is an exploded view of the exemplary embodiment of the intervertebral implant according to the invention shown in FIG. 1.
Figure 6:
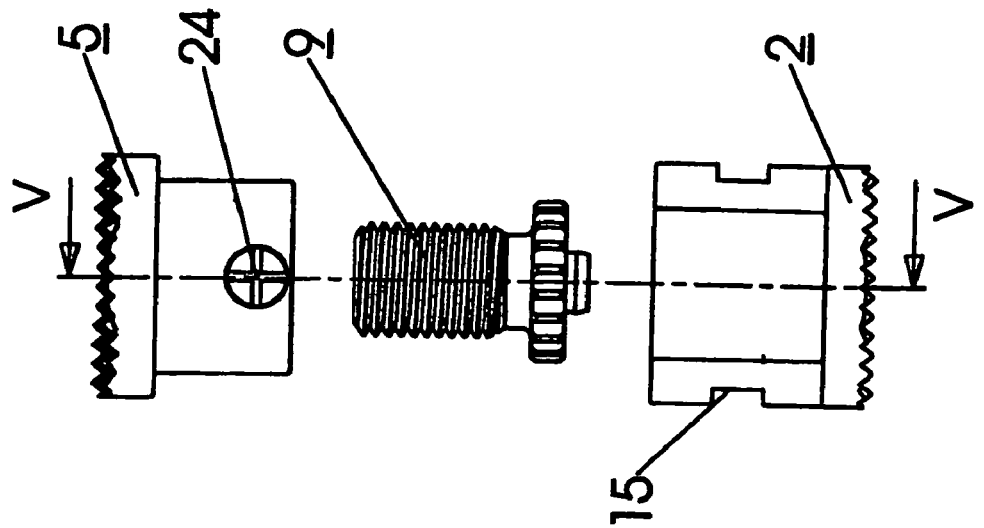
FIG. 6 is an exploded view of the embodiment of the intervertebral implant according to the invention shown in FIGS. 1 to 5.
Figure 5:
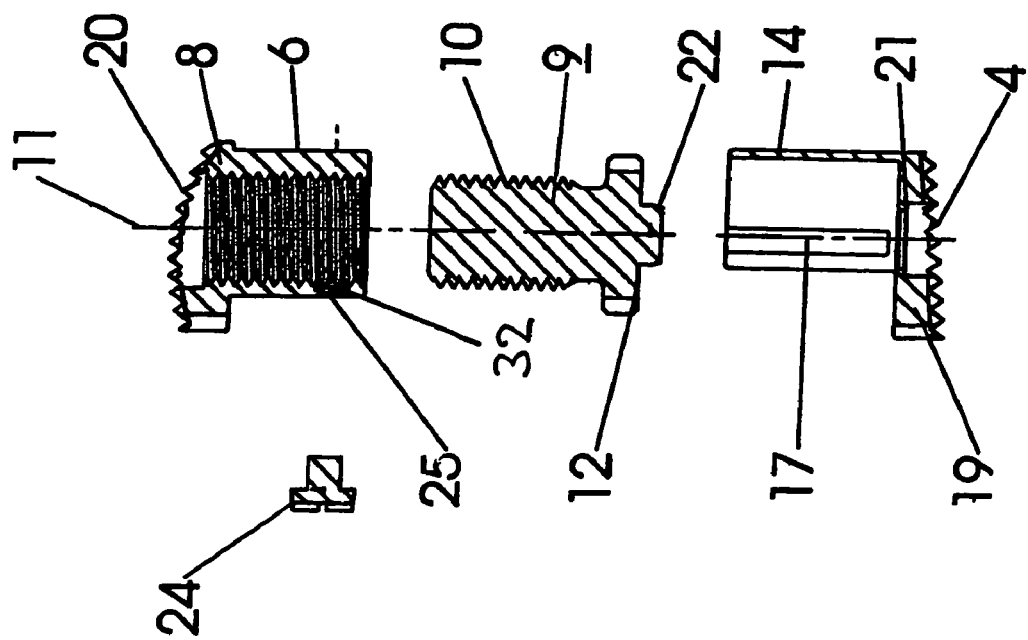
FIG. 5 is a section parallel to the central axis, of an exploded view of the embodiment of the intervertebral implant according to the invention shown in FIGS. 1 to 4.

The lower implant part 2 comprises a posterior cavity 3 that is coaxial with the central axis 11 and cylindrical, having a mantle 14 that is open at the anterior (FIG. 2). The upper implant part 5 has a circular-cylindrical shaft 6 that is coaxial with the central axis 11, having a coaxial bore 30 having an inside thread 7 (FIG. 3). The circular-cylindrical shaft 6 extends into the cavity 3 of the lower implant part 2 and is displaceable in the cavity 3, parallel to the central axis 11. The two implant parts 2; 5 are secured relative to one another about the central axis 11, to prevent rotation, whereby to secure them against rotation, of the upper part 5 relative to the lower part 2, the circular-cylindrical shaft 6 of the upper implant part 5 has two wedges 16 placed parallel to the central axis 11 and laterally on the shaft 6. The mantle 14 of the lower implant part 2 has two guide slots 17, placed laterally, on its inside, which serve to accommodate the wedges 16. The wedges 16 are mounted in the guide slots 17 so as to be axially displaceable. In this connection, the circular-cylindrical shaft 6 on the upper implant part 5 has a smaller diameter than the cavity 3 of the lower implant part 2, so that the two implant parts 2; 5 are in contact with one another only by means of the two wedges 16 in the guide slots 17.

Furthermore, the intervertebral implant 1 comprises a threaded spindle 9 having an outside thread 10. This threaded spindle 9 is disposed coaxial to the central axis 11 and has a lower surface 12 that stands perpendicular to the central axis 11 and rests on the lower implant part 2. The outside thread 10 of the threaded spindle 9 is configured to be complementary to the inside thread 7 in the bore 30 made in the upper implant part 5, so that the threaded spindle 9 can be screwed into the inside thread 7. By turning the threaded spindle 9 about the central axis 11, the two implant parts 2; 5 are therefore displaced relative to one another, parallel to the central axis 11, so that the distance between the two apposition parts 4; 8 can be changed in stepless manner. Furthermore, the threaded spindle 9 is connected with the lower implant part 2 so that it is fixed axially but can be moved rotationally about the central axis 11. Here, this connection comprises a clip connection, which is implemented by means of a torus-shaped undercut 21 on the journal 36 (FIG. 3) disposed on the lower end 26 of the threaded spindle 9, at the end position, and a circular bead 22 that is placed in the bore 35 that is also coaxial to the central axis 11. By means of the circular bead 22 in the bore 35 that can engage in the undercut 21 on the journal 36, the threaded spindle 9 and the lower implant part 2 are firmly connected with one another axially.

Between the outside thread 10 and the end-position journal 36, the threaded spindle 9 comprises a gear crown 23 that is coaxial to the central axis 11. Furthermore, two slots 15 that run perpendicular to the central axis 11 are placed laterally on the mantle 14. To adjust the distance between the apposition parts 4; 8 by means of rotating the threaded spindle 9 about the central axis 11, the front part, which is fork-shaped, for example, of an instrument is positioned in the slots 15 and the instrument is supported. The instrument preferably comprises rotary drive means at the back, for example a rotating handle, which is connected with a deflection gear mechanism disposed at the front end of the instrument, for example, by means of an axle. The rotation movement of the rotating handle is converted into a rotation movement having an axis of rotation that stands perpendicular to the axis of the rotating handle, for example, by means of the deflection gear mechanism, so that when the instrument is in position, the end-position gear wheel of the deflection gear mechanism can be brought into engagement with the gear crown 23.

The anterior side surfaces 41; 82 of the two apposition parts 4; 8 are each structured with a circular recess 13; 18. The recesses 13; 18 are suitable for the accumulation of spongiosa.

A bore 32 having an inside thread 25 (FIG. 5) passes through the outer wall of the shaft 6, crosswise to the central axis 11, in such a manner that the threaded spindle 9 can be locked in place in the upper implant part 5 by means of a setting screw 24 that can be screwed into the inside thread 25. The setting screw 24 serves to secure the threaded spindle 9 against rotation, after the desired distance between the apposition parts 4; 8 has been set.

What is claimed is:

1. An intervertebral implant insertable into an intervertebral disc space between adjacent upper and lower vertebral bodies, the implant having a central axis and comprising:
    a lower implant part having an apposition surface intended to rest against the adjacent lower vertebral body, the lower implant part including a hollow-cylinder cavity defining an inner surface, the lower implant part having at least one guide slot formed in the inner surface;
    an upper implant part having an essentially circular-cylindrical shaft including a bore with an inside thread and an apposition surface intended to rest against the adjacent upper vertebral body, the shaft including at least one wedge extending therefrom, the at least one wedge being parallel to the central axis, the bore passing axially through the shaft, parallel to the central axis, the at least one wedge being axially received within the at least one guide slot so that said lower and upper implant parts are secured relative to one another, to prevent rotation about the central axis, wherein the circular-cylindrical shaft has a circumference that is spaced apart from the inner surface of the cavity so that the upper implant part and the lower implant part only contact one another via the at least one wedge contacting the at least one guide slot; and
    a threaded spindle, insertable into the bore formed in said upper implant part and connected with said lower implant part, the threaded spindle having an outside thread that interacts with said inside thread and a gear crown that is concentric to the central axis, wherein:
    said lower and upper implant parts and said threaded spindle are disposed to be coaxial along the central axis; and
    the distance between said two apposition parts can be changed in a stepless manner by rotating said threaded spindle, said threaded spindle being fixed in place on said lower implant part so as to be fixed axially but movable rotationally, by means of a clip connection.

2. The intervertebral implant according to claim 1, wherein the clip connection comprises elastically deformable segments on said threaded spindle and on said lower implant part.

3. The intervertebral implant according to claim 2, wherein the clip connection is formed from a torus-shaped undercut in said threaded spindle and a corresponding ring-shaped bead on said lower implant part.

4. The intervertebral implant according to claim 1, wherein said threaded spindle has a lower surface perpendicular to the central axis and rests on said lower implant part.

5. The intervertebral implant according to claim 1, wherein the lower implant part has at least one slot perpendicular to the central axis for positioning and supporting an instrument relative to the gear crown.

6. The intervertebral implant according to claim 1, wherein the two apposition surfaces each have an anterior side surface, the cavity is open at the anterior.

7. The intervertebral implant according to claim 1, wherein the inside thread and the outside thread are configured to be self-locking.

8. The intervertebral implant according to claim 7, wherein a pitch of the inside thread and the outside thread lies in the range of 0.5-1.0 mm.

9. The intervertebral implant according to claim 8, wherein a pitch of the inside thread and the outside thread lies in the range of 0.6-0.8 mm.

10. The intervertebral implant according to claim 1, wherein both the inside thread and the outside thread are configured to be right-hand threads.

11. The intervertebral implant according to claim 1, wherein the two apposition surfaces each have an anterior side surface which is provided with a circular recess, in each instance, which is suitable for the accumulation of spongiosa.

12. The intervertebral implant according to claim 1, wherein the two apposition surfaces are configured as plate-shaped elements that stand crosswise to the central axis.

13. The intervertebral implant according to claim 12, wherein the apposition surfaces are disposed non orthogonal to the central axis and enclose an angle of 80 degrees to 89 degrees with the central axis.

14. The intervertebral implant according to claim 13, wherein the two apposition surfaces enclose an angle of 2 degrees to 20 degrees with one another.

15. The intervertebral implant according to claim 12, wherein the two apposition surfaces each have two lateral side surfaces parallel to sagittal direction, and at least one of the two apposition surfaces has a dome that runs in the sagittal direction.

16. The intervertebral implant according to claim 1, wherein the shaft has a bore disposed crosswise to the central axis, the bore having a thread for threadably engaging a set screw.

17. The intervertebral implant according to claim 1, wherein the implant is manufactured from PEEK.

* * * * *